Nov. 5, 1974 G. HOWARD, JR Plant Pat. 3,645
KALANCHOE PLANT
Filed Oct. 16, 1973
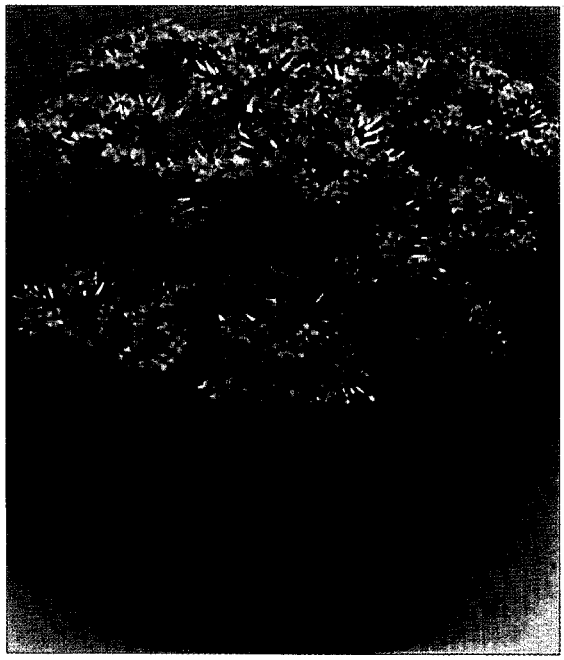
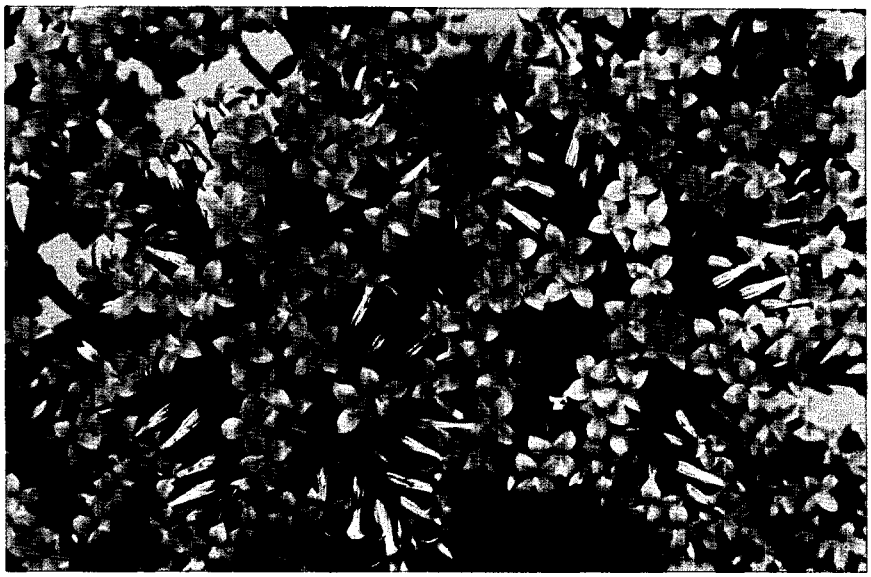

United States Patent Office

Plant Pat. 3,645
Patented Nov. 5, 1974

3,645
KALANCHOE PLANT

Grady Howard, Jr., Amarillo, Tex., assignor of a fractional part interest to J and L Plants, Incorporated, doing business as Howard Greenhouses, Canyon, Tex.

Filed Oct. 16, 1973, Ser. No. 406,916
Int. Cl. A01h 5/00
U.S. Cl. Plt.—68 1 Claim The present invention relates to a new and distinct variety of kalanchoe plant which was originated by me by crossing the kalanchoe variety known as "Tom Thumb" (unpatented) with an unnamed and unpatented seedling of unknown parentage, which I selected from crosses of various kalanchoe varieties which I had collected and accumulated over a period of some five years during the course of my experimental breeding and developing operations.

As the result of this particular breeding, I have produced a new and improved kalanchoe variety which is distinguished from its parents and from all other kalanchoe varieties of which I am aware, as evidenced by the following unique combination of principal characteristics which are outstanding therein and which represents a new form and flower color in the broad field of commercially valuable kalanchoes:

(1) A branching and medium tall habit of growth;
(2) Attractive Fern Green foliage of medium size;
(3) A uniform blooming date and fast photo-periodic response;
(4) Production of a profusion of relatively large flowers which are borne moderately close to the foliage;
(5) A distinctive and attractive Crimson flower color;
(6) Long-lasting qualities; and
(7) The ability to be brought into flower all year around, even under high night temperatures of summer.

Asexual reproduction of my new kalanchoe variety by cuttings, as performed by me in my greenhouses at Amarillo, Texas, shows that the foregoing characteristics and distinctions come true and are established and transmitted through succeeding propagations.

The accompanying drawing shows a typical blooming plant specimen of my new variety, as well as some of the blooms on a larger scale than in the view of the whole plant, as depicted in color as nearly true as it is reasonably possible to make the same in a color illustration of this character.

The following is a detailed description of my new kalanchoe variety, with color terminology in accordance with the Exotica Horticultural Color Guide, published by Roehrs Company, except where general color terms of ordinary dictionary significance are obvious:

Parentage: Seedling.
*Seed parent.*—An unnamed seedling of unknown parentage.
*Pollen parent.*—"Tom Thumb."
Propagation: Holds its distinguishing characteristics through succeeding propagations by cuttings.
Locality Where Grown and Observed: Amarillo and Canyon, Texas.
Plant:
*Form.*—Much-branched; upright; compact.

*Growth habit.*—Upright; branching; compact; averages from about 11 inches to 14 inches tall.
*Rooting habit.*—Roots easily in 10 to 14 days from stem cuttings, with many fibrous roots.
*Blooming habit.*—Compound umbel.
*Blooming season.*—Normally about December 8, but is photo-periodic and can be brought into bloom all year round.
Foliage:
*Size.*—Medium.
*Quantity.*—Normal.
*Color.*—New foliage: Upper side—Fern Green, No. 84—. Under side—Fern Green, No. 83—. Old foliage: Upper side—Fern Green, No. 83+. Under side—Fern Green, No. 83—.
*Shape.*—Generally elliptic, with base being more obtuse than in a regular elliptic leaf; leaves have a tendency to curl upward at margins as they mature.
*Texture.*—Upper side—Glossy; smooth. Under side—Smooth.
*Margin.*—Orentate on young foliage, but becoming more undulate as leaves mature.
Disease Resistance: Good resistance to usual diseases to which some kalanchoe varieties are normally subject, as determined by comparison with other varieties grown in greenhouses at Amarillo and Canyon, Texas.
Flowers: Perfect.
*Diameter.*—About ¾ inch.
*Depth.*—About 7/16 inch.
*Petals.*—Length—About 5/16 inch. Width—About 3/16 inch.
*Form.*—Perigynous; 4-parted corolla and pistil; 8 stamens; section petals united; ovary inferior.
*Color.*—Upper side—Newly open: Near Crimson, No. 32 under natural light. Older petals: Near Crimson, No. 32 under natural light. Under side—Carmine, No. 31.
*Blooming period.*—From about 4 to 6 weeks.
Hardness: Satisfactorily withstands greenhouse temperatures ranging from about 60° F. to 100° F.
General Observations: This new kalanchoe variety offers a unique and exciting flower color, with the flowers borne in profuse mass on medium stems, combined with attractive foliage of medium size and with long keeping qualities of the flowers and foliage.

I claim:

1. A new and distinct variety of kalanchoe plant, substantially as herein shown and described, characterized particularly as to novelty by the unique combination of a branching and medium tall habit of growth, attractive Fern Green foliage of medium size, a uniform blooming date and fast photo-periodic response, production of a profusion of relatively large flowers which are borne moderately close to the foliage, a distinctive and attractive Crimson flower color, long-lasting qualities, and the ability to be brought into flower all year round, even under high night temperatures of summer.

No references cited.

ROBERT E. BAGWILL, Primary Examiner